United States Patent
McKimpson et al.

(10) Patent No.: US 9,732,838 B2
(45) Date of Patent: Aug. 15, 2017

(54) GEARBOX COMPONENT AND LUBRICANT CONDITION MONITORING SYSTEM

(71) Applicant: Caterpillar Inc., Peoria, IL (US)

(72) Inventors: Marvin Grendel McKimpson, Metamora, IL (US); Richard Andrew Carpenter, Chillicothe, IL (US)

(73) Assignee: Caterpillar Inc., Peoria, IL (US)

( * ) Notice: Subject to any disclaimer, the term of this patent is extended or adjusted under 35 U.S.C. 154(b) by 0 days.

(21) Appl. No.: 14/861,150

(22) Filed: Sep. 22, 2015

(65) Prior Publication Data

US 2017/0082188 A1 Mar. 23, 2017

(51) Int. Cl.
| | | |
|---|---|---|
| *G01M 17/00* | (2006.01) | |
| *F16H 57/01* | (2012.01) | |
| *F16H 57/04* | (2010.01) | |
| *G01N 33/28* | (2006.01) | |
| *G05B 23/02* | (2006.01) | |
| *F03D 17/00* | (2016.01) | |

(52) U.S. Cl.
CPC .............. *F16H 57/01* (2013.01); *F03D 17/00* (2016.05); *F16H 57/0405* (2013.01); *G01N 33/2888* (2013.01); *G05B 23/0283* (2013.01); *F16H 2057/012* (2013.01)

(58) Field of Classification Search
CPC . F16H 57/01; F16H 57/0405; F16H 2057/012
USPC ...... 701/29.4, 31.4, 32.1, 3; 324/658, 207.2, 324/242
See application file for complete search history.

(56) References Cited

U.S. PATENT DOCUMENTS

| | | | |
|---|---|---|---|
| 5,566,092 A | 10/1996 | Wang et al. | |
| 6,776,261 B2 | 8/2004 | Eriksen et al. | |
| 8,214,099 B2 * | 7/2012 | Scheffel | G01M 13/02 701/32.1 |
| 8,356,207 B2 * | 1/2013 | Hosek | G05B 23/0235 702/184 |
| 8,502,527 B2 * | 8/2013 | Bradley | G01R 33/072 324/207.2 |
| 2008/0177436 A1 * | 7/2008 | Fortson | G05B 23/0221 701/31.4 |
| 2009/0157235 A1 * | 6/2009 | Stebbins | B64F 1/22 701/3 |

(Continued)

FOREIGN PATENT DOCUMENTS

| | | |
|---|---|---|
| CN | 204359538 | 5/2015 |
| GB | 2491045 | 11/2012 |

*Primary Examiner* — Shardul Patel (74) *Attorney, Agent, or Firm* — Finnegan, Henderson, Farabow, Garrett & Dunner, LLP (57) ABSTRACT

A monitoring system for a gearbox having at least one rotational component having a design lifetime and at least one design parameter is disclosed. The monitoring system may include a first sensor configured to generate a first signal indicative of a speed associated with the at least one rotational component, a second sensor configured to generate a second signal indicative of a torque associated with the rotational component, and a controller electronically connected to the first and second sensors. The controller may be configured to determine a remaining lifetime of the at least one rotational component based on the design lifetime, the at least one design parameter, and the first and second signals over a period of operating time, and generate a maintenance signal based on the remaining lifetime.

16 Claims, 2 Drawing Sheets

(56) References Cited

U.S. PATENT DOCUMENTS

| | | | |
|---|---|---|---|
| 2012/0025526 A1* | 2/2012 | Luo | F03D 15/00 |
| | | | 290/44 |
| 2014/0347043 A1* | 11/2014 | Chana | G01M 13/021 |
| | | | 324/242 |
| 2015/0292857 A1* | 10/2015 | Lu | G01B 7/30 |
| | | | 324/658 |

* cited by examiner

GEARBOX COMPONENT AND LUBRICANT CONDITION MONITORING SYSTEM

TECHNICAL FIELD

The present disclosure relates generally to a monitoring system and, more particularly, to a gearbox component and lubricant condition monitoring system.

BACKGROUND

Many mobile and stationary machines employ drive systems that transmit mechanical energy from an input end to an output end for performing various tasks. Where control of certain drive system output parameters (e.g., speed, torque, direction of rotation or travel, etc.) is desired, mechanical devices, such as gearboxes, are commonly connected between the input end and the output end of the drive system. A gearbox typically includes a number of components that work together to transmit power, such as gears, shafts, and bearings, that are protected from their surroundings in a sealed container. The components within a gearbox are usually immersed in or supplied with a lubricant to reduce friction and keep the internal components cool during operation. Over time, the components within the gearbox can wear and/or fail, and the lubricant can degrade or become contaminated with debris, thereby requiring periodic maintenance and/or replacement.

Gearbox maintenance and replacement requires that the associated machine be temporarily taken out of service, which can decrease productivity. One way to reduce loss of productivity is to reduce the likelihood of unexpected component failures by performing regularly scheduled maintenance during periods of anticipated downtime. However, certain operating practices and harsh operating conditions can expedite the wearing of gearbox components and lubricant, resulting in a need for unscheduled maintenance and/or repairs. Predicting when unscheduled maintenance or repairs will be needed can be difficult due to widely varying operating practices and jobsite conditions.

One attempt to monitor the health and performance of a gearbox is described in U.S. Patent Application Publication No. 2012/0025526 A1 (the '526 publication) of Luo et al. that published on Feb. 2, 2012. The '526 publication describes a gearbox monitoring system for a wind turbine having a rotating blades attached to a shaft for driving a generator. The shaft is connected to the generator via a gearbox. A number of sensors associated with the gearbox measure gearbox performance during operation of the wind turbine. These sensors include tachometers that measure shaft speed, strain gauges that measure torque experienced by the turbine, accelerometers attached to bearings that detect mechanical vibrations, bearing temperature sensors, and an oil particle counter that measures debris within a gearbox lubricant. A computer connected to each of the sensors compares signals from the sensors to design limitations and generates a warning when the operating conditions exceed the design limitations. The controller may also determine that a gearbox component is damaged when the signals from the sensors exceed a threshold and automatically shut down the turbine when damage is detected.

Although the system of the '526 publication may be able to determine when the performance of a gearbox exceeds its design parameters or has been damaged, it may not be optimum. In particular, the system of the '526 publication may allow an operator to know when the gearbox is in need of maintenance or repair only after damage has occurred. Further, the system of the '526 publication may only convey the health of the gearbox in terms of whether or not current performance parameters are within design limitations and may not account for other aspects and/or factors of gearbox health.

The monitoring system of the present disclosure solves one or more of the problems set forth above and/or other problems of the prior art.

SUMMARY

In one aspect, the present disclosure is directed to a monitoring system for a gearbox having at least one rotational component having a design lifetime and at least one design parameter. The monitoring system may include a first sensor configured to generate a first signal indicative of a speed associated with the at least one rotational component, a second sensor configured to generate a second signal indicative of a torque associated with the rotational component, and a controller electronically connected to the first and second sensors. The controller may be configured to determine a remaining lifetime of the at least one rotational component based on the design lifetime, the at least one design parameter, and the first and second signals over a period of operating time, and generate a maintenance signal based on the remaining lifetime.

In another aspect, the present disclosure is directed to a method of monitoring a gearbox having at least one rotational component having a design lifetime and at least one design parameter. The method may include determining a speed associated with the at least one rotational component, determining a torque associated with the rotational component, and determining a remaining lifetime of the at least one rotational component based on the design lifetime, the at least one design parameter, and the speed and the torque associated with the at least one rotational component over a period of operating time. The method may further include generating a maintenance signal based on the remaining lifetime.

In yet another aspect, the present disclosure is directed to a monitoring system for a gearbox having at least one rotational component having a design lifetime and at least one design parameter. The monitoring system may include a first sensor configured to generate a first signal indicative of a speed associated with the at least one rotational component, a second sensor configured to generate a second signal indicative of a torque associated with the rotational component, a third sensor configured to generate a third signal indicative of a vertical load on the at least one rotational component, and a controller electronically connected to the first, second, and third sensors. The controller may be configured to determine a remaining lifetime of the at least one rotational component based on the design lifetime, the at least one design parameter, and the first, second, and third signals over a period of operating time. The at least one design parameter may include one or more of a design torque, a design speed, and a design load. The controller may be further configured to generate a maintenance signal based on the remaining lifetime, wherein the maintenance signal is indicative of a need to perform gearbox maintenance before the gearbox reaches the design lifetime.

DETAILED DESCRIPTION

Figure 1:
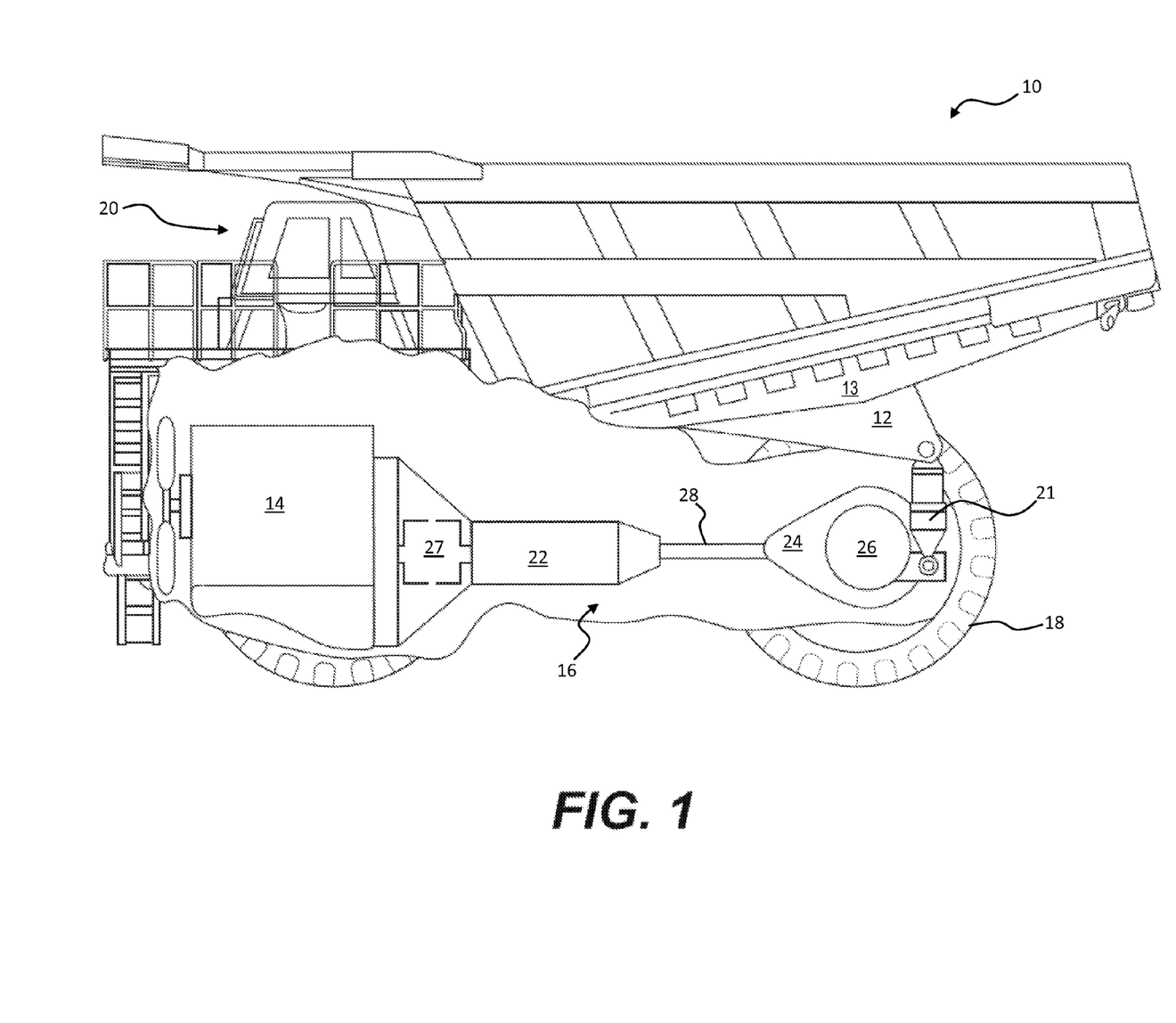
FIG. 1 is a diagrammatic illustration of a machine incorporating an exemplary disclosed monitoring system.

FIG. 1 illustrates an exemplary mobile machine 10. Machine 10 may perform some type of operation associated with an industry such as mining, construction, farming, transportation, or any other industry. For example, machine 10 may be an earth moving machine such as an off-highway haul truck, a wheel loader, a motor grader, or any other suitable earth moving machine. Machine 10 may alternatively embody an on-highway vocational truck, a passenger vehicle, or any other operation-performing machine. Although machine 10 is embodied in FIG. 1 as an off-highway haul truck, it understood that machine 10 may embody a stationary type of machine such as a drilling system, a pumping system, a wind turbine, a wave energy converter, or any other machine having a mechanical energy input and/or output. Machine 10 may include, among other things, a frame 12 connected to a body 13 of machine 10, a power source 14 mounted to frame 12, a drive system 16 driven by power source 14, one or more traction device(s) 18 connected to frame 12 and driven by drive system 16, and an operator station 20 mounted to frame 12 for controlling operations of machine 10.

Power source 14 may be configured to produce a power output and may be an internal combustion engine. For example, power source 14 may be a diesel engine, a gasoline engine, a gaseous fuel-powered engine, or any other type of engine. It is understood that power source 14 may alternatively be a non-combustion power source such as, for example, a battery, a fuel cell, a motor (e.g., driven by electricity, wind, waves, a fluid current, etc.), or any other type of non-combustion source of power.

A suspension device 21 may connect drive system 16 to frame 12 and allow for cushioned movement of frame 12 relative to drive system 16. Suspension device 21 may include a resilient component (e.g., a spring, a flexible fluid chamber, hydraulic or pneumatic cylinder, etc.) that contracts and expands in response to varying vertical loads on frame 12. For example, suspension device 21 may include a mechanical spring (e.g., a leaf spring, a coil spring, etc.) and/or a fluid system containing a compressible fluid (e.g., air) and/or a non-compressible fluid (e.g., hydraulic fluid, oil, etc.). Suspension device 21 may contract in response to increasing loads (i.e., forces tending to urge frame 12 and drive system 16 toward each other) and expand in response to decreasing loads. For instance, when machine 10 is filled with payload material, the weight of the material may apply a vertical load $L_V$ on suspension device 21, causing it to contract. When the material is emptied from machine 10, suspension device 21 may expand to its previous position. In another instance, when machine 10 traverses rugged terrain that causes machine 10 to bounce or be jolted in the vertical direction, suspension device 21 may contract when machine 10 is suddenly jolted up or down, and expand to its previous position under the force of its resilient component.

Drive system 16 may be configured to transfer the power output from power source 14 to traction devices 18 via one or more gearboxes 22-26. Gearboxes 22-26 may be configured to receive the output of power source 14 and collectively drive traction devices 18 with desired output characteristics. Gearboxes 22-26 may each include at least one rotational component (e.g., a gear, a bearing, a shaft, etc.— not shown) contained within a housing and configured to convert, transfer, and/or transmit mechanical power from an input end to an output end.

Gearboxes 22-26 may include a transmission 22, a differential 24, and one or more final drive unit(s) 26 (only one shown in FIG. 1). Although they are shown as separate units in FIG. 1, gearboxes 22-26 may alternatively be combined in a single axle or rear end assembly. Drive system 16 may include fewer or different types of gearboxes than gearboxes 22-26 mentioned above. For example, in other embodiments, drive system 16 may also or alternatively include a front axle assembly having one or more final drive units connected via a front differential and/or a transfer case to transmission 22 or power source 14 for driving one or more front-end traction devices. It is understood that other configurations of drive system 16 may be possible.

Transmission 22 may include numerous components that interact to transmit power from power source 14 to traction device(s) 18. For example, transmission 22 may embody a multi-speed, bidirectional, mechanical transmission having a plurality of gears (not shown) that are selectable to change the output speed and torque of transmission 22. The gears and other components (e.g., bearings, seals, valves, etc.) of transmission 22 may be lubricated and cooled by a lubricant system (not shown) connected to transmission 22. The lubricant system may include a sump for holding a lubricant (e.g., a lubricant oil or other fluid) a pump, a filter, and a cooling device (e.g., a heat exchanger). Over time, debris particles and other contaminants may accumulate in the lubricant of transmission 22. The debris particles may include wear particles generated within transmission 22 (i.e. particles shed by the gears and bearings caused by wear and/or failure) and external contaminants (e.g., dirt, sand, dust, fluid from other fluid circuits etc.). Accumulation of debris particles over time and/or failure of bearings and seals may necessitate periodic replacement of the lubricant and/or transmission 22.

Transmission 22 may be a single-clutch automatic transmission, and may be coupled to power source 14 via a torque converter 27. In other embodiments, transmission 22 may embody another type of automatic transmission, such as a multi-clutch automatic transmission. Transmission 22 may alternatively embody a manual-shift transmission and include a number of gears connectable to power source 14 via a manually operated clutch and gear selector. It is understood that transmission 22 may embody any suitable type of transmission for transferring mechanical energy between power source 14 and traction device(s) 18.

Differential 24 may include a number of rotational components (e.g., gears, bearings, shafts, etc.) that interact to transmit power from transmission 22 to other components of drive system 16. For example, differential 24 may be configured to receive power from transmission 22 via a shaft 28 that rotates at a speed and with an amount of torque determined by settings of transmission 22. Differential 24 may be configured (e.g., via a set of gears) to create rotation around an axis that is not parallel with shaft 28 (e.g., perpendicular to shaft 28).

Differential 24 may also contain a lubricant for cooling and reducing wear of the gears and bearings therein. The lubricant may be delivered to differential 24 via an external lubricant system, which may include a sump, a pump, a filter, a cooling device, etc. Alternatively, the lubricant within differential 24 may be contained solely within differential 24. Over time, wear particles and external debris particles (e.g., dirt, other fluids, etc.), may contaminate the lubricant and necessitate periodic replacement of the lubricant or components of differential 24.

Final drive 26 may include a number of rotational components (e.g., gears, bearings, shafts, etc.) that interact to transmit power from differential 24 to traction device(s) 18. Final drive 26 may include a set of gears (e.g., planetary gears or other types of gears) having a gear ratio configured to reduce the speed and increase the torque output of traction device(s) 18. A separate final drive 26 may be assigned to each traction device 18.

Final drive 26 may also contain a lubricant for cooling and reducing wear of the gears and bearings therein. The lubricant may be delivered to final drive 26 via a dedicated lubricant system, which may include a sump, a pump, a filter, a cooling device, etc. Alternatively, final drive 26 may share the lubricant system of differential 24 and/or transmission 22. In some embodiments, the lubricant for final drive 26 may be contained solely within final drive 26. Over time, debris particles, such as wear particles (e.g., particles shed from gears, bearings, etc.) and external debris particles (e.g., dirt, other fluids, etc.), may contaminate the lubricant and necessitate periodic replacement of the lubricant or components of final drive 26.

Each rotational component within gearboxes 22-26 may have an associated design lifetime $\theta_D$ and at least one associated design parameter that may be used by maintenance personnel to estimate a remaining lifetime of each rotational component after an elapsed period of operating time and develop a regular maintenance schedule. The design lifetime $\theta_D$ of a rotational component may be an amount of time or other performance metric, such as a distance, number of revolutions, number of cycles, etc., over which the component is designed or expected to function properly under the at least one design parameter.

Design parameters may be one or more particular operating parameters (e.g., torque, rotational or linear speed, radial or axial load, temperature etc.) that the rotational component is designed to withstand and achieve its design lifetime. For example, a rotational component (e.g., a gear or bearing) driven with a given torque $\tau$ at a given speed s under a given radial load L may be designed or expected to function properly for a certain amount of operating time before it begins to function improperly or fail. When the operating parameters remain steady and equal to the design parameters, a remaining lifetime $\theta_R$ of the rotational component may be determined as a difference between the design lifetime $\theta_D$ and an elapsed operating time, such as a time since a previous maintenance visit. As operating parameters vary, the remaining lifetime $\theta_R$ of the rotational component may be a function of one or more operating parameters and may be greater than or less than a threshold time period, such as an amount of time until a next regularly scheduled service date.

Figure 2:
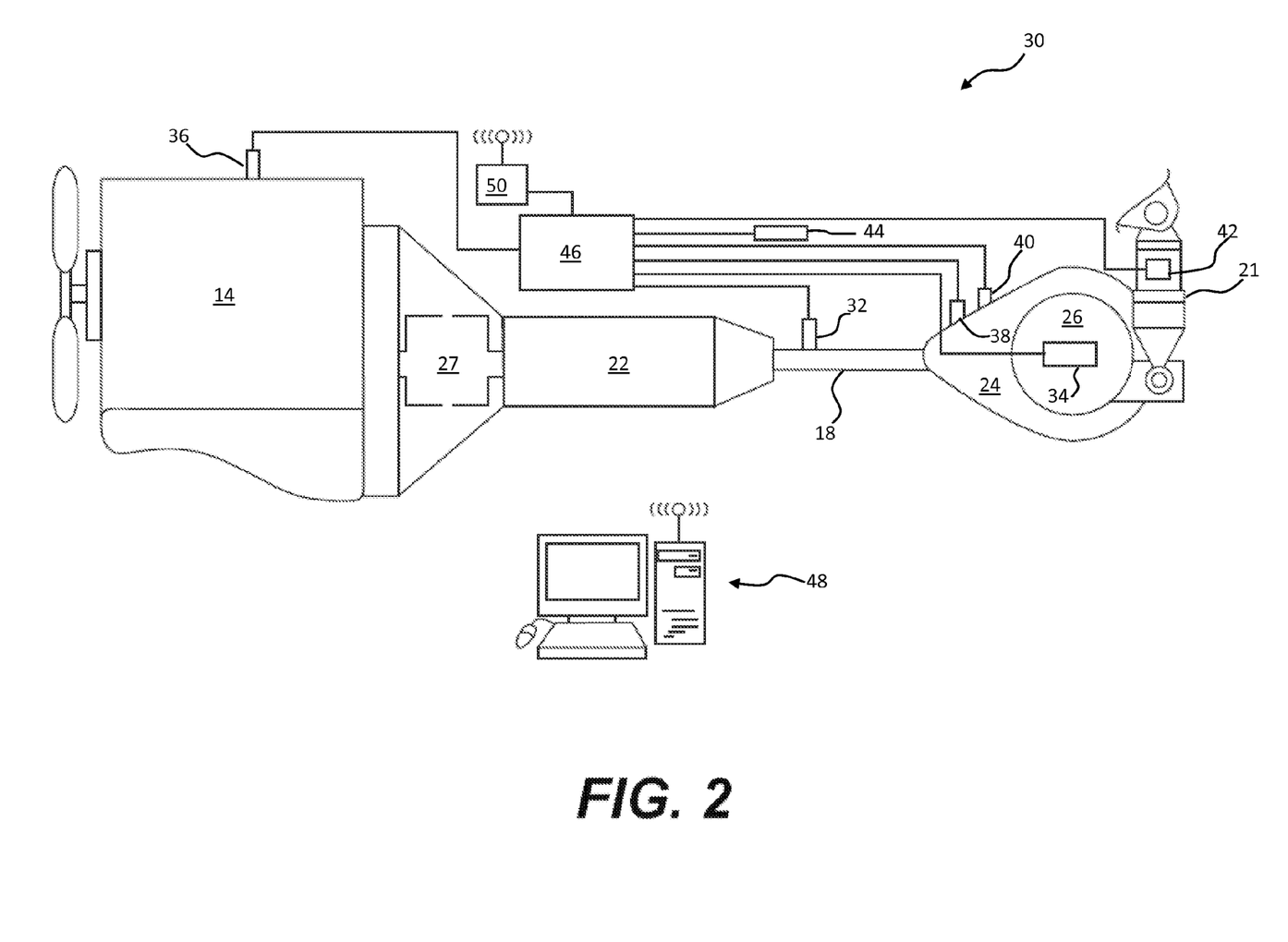
FIG. 2 is a diagrammatic illustration of an exemplary controller and data inputs that may be used in conjunction with the monitoring system of FIG. 1.

FIG. 2 shows a gearbox monitoring system 30 that may be associated with one or more of gearboxes 22-26 and configured to estimate the remaining lifetime $\theta_R$ of the rotational components with the associated gearboxes 22-26. Gearbox monitoring system 30 may include a number of sensors 32-36, 40-44 and a lubricant monitoring system associated with one or more of gearboxes 22-26 and positioned throughout drive system 16 and/or machine 10. Sensors 32-36, 40-44 and lubricant monitoring system 38 may be configured to generate signals indicative of operating parameters of one or more of power source 14, drive system 16 (e.g., gearboxes 22-26), suspension device 21, and the ambient conditions around machine 10. Sensors 32-36, 40-44 and lubricant monitoring system 38 may be electronically connected to a controller 46 configured to receive signals from each sensors 32-36, 40-44 and lubricant monitoring system 38. Controller 46 may be configured to determine the remaining lifetime of the rotational components within gearboxes 22-26. Data received and generated by controller 46 may be transmitted to an offboard entity, such as an offboard computer 48, via a communication device 50 electronically connected to controller 46.

Gearbox monitoring system 30 may include a first speed sensor 32 configured to generate a signal indicative of the speed s associated with at least one rotational component of gearboxes 22-26. Although speed sensor 32 is shown in FIG. 2 as being associated with shaft 28, it is understood that additional speed sensors may be associated with other components of drive system 16. The signal generated by speed sensor 32 may be indicative of an input speed to one or more of gearboxes 22-26 and/or an associated rotational component. That is, speed sensor 32 may be configured to detect the rotational speed of a component of drive system 16 (e.g., an output speed of transmission 22, a speed of shaft 28, an input speed of differential 24, etc.) that may be used to determine the input speed of another component of drive system 16 (e.g., an input speed of final drive 26, the speed of a rotational component within final drive 26 etc.) based on associated gear ratios.

In some embodiments, gearbox monitoring system 30 may also or alternatively include a second speed sensor 34 configured to generate a signal indicative of the speed s associated with at least one rotational component of gearboxes 22-26. Speed sensor 34 may be, for example, a wheel speed sensor associated with traction device 18 (referring to FIG. 1). The signal generated by speed sensor 34 may be indicative of a rotational speed of traction device 18 and may be used to determine the speed s of a rotational component of gearboxes 22-26 based on, for example, a radius of traction device 18 and gear ratios associated with gearboxes 22-26. It is understood that other speed sensors positioned at other locations throughout drive system 16 may be used.

Gearbox monitoring system 30 may also include a torque sensor 36 configured to generate a signal indicative of or used to determine a torque $\tau$ associated with one or more rotational components of gearboxes 22-26. For example, torque sensor 36 may include one or more sensors, such as an engine speed sensor used in conjunction with an engine speed-torque map stored within controller 46. That is, torque sensor 36 may generate an engine speed signal that is indicative of the engine output torque via a map or lookup table. The map or lookup table may correlate engine speed with torque in conjunction with other parameters, such as a percent engine load (e.g., based on fuel flow rate or other fuel consumption parameter, throttle position, etc.) and the rotational speed of other components (e.g., torque converter 27, transmission 22, final drive 26, etc.). For example, torque $\tau$ may be determined based on engine torque (e.g., based on an engine torque map) and an input speed to output speed ratio of torque convertor 27. Other ways of determining torque $\tau$ may be used, if desired.

In some embodiments, torque sensor 36 may include one or more additional sensors associated with one or more other components of drive system 16 (e.g., torque converter 27, transmission 22, shaft 28, final drive 26, etc.). For example, torque sensor 36 may include an additional sensor configured to determine an input speed of torque converter 27. The input speed may alternatively be determined based on the signal from the engine speed sensor. Torque sensor 36 may also include an additional sensor configured to generate a signal indicative of the output speed of torque converter 27.

The output speed of torque converter 27 may be determined via a sensor configured to measure the output speed of torque converter 27 or another component (e.g., transmission 22, final drive 26, etc.) from which the output speed of torque converter 27 can be determined.

In some embodiments, torque sensors 36 may be configured to directly measure torque values. For example, torque sensor 36 may be a strain gauge, a non-contact torque transducer (e.g., magnetic sensor, telemetry-based sensor, etc.), or another type of torque sensor attached to or associated with a component of drive system 16. The torque $\tau$ measured from one component of drive system 16 may be used to determine a torque input to another component of drive system 16 or rotational component of gearboxes 22-26 based on associated gear ratios and/or speed measurements.

Gearbox monitoring system 30 may also include a lubricant monitoring system 38 configured to generate one or more signals indicative of lubricant condition associated with gearboxes 22-26. For example, lubricant monitoring system 38 may be configured to measure the concentration and size of debris particles in the lubricant of gearboxes 22-26. As the rotational components (e.g., gears, bearings, etc.) within gearboxes 22-26 wear and/or fail and shed debris particles, the concentration of debris particles in the lubricant may be indicative of the remaining lifetime $\theta_R$ of the rotational components and/or the lubricant therein. Although lubricant monitoring system 38 is associated with final drive 26 in the example of FIG. 2, it is understood that lubricant monitoring system 38 may be associated with any one or more of gearboxes 22-26.

Lubricant monitoring system 38 may include a particle sensor, such as an optical sensor configured to use a light source to illuminate and count individual particles passing through a detection chamber. Lubricant monitoring system 38 may be further configured to determine a size of each counted particle and tabulate counted particles according to their size or size distribution among a range of sizes. For example, lubricant monitoring system 38 may be configured to count debris particles ranging from 1 to 100 µm. It is understood, however, that lubricant monitoring system 38 may be configured to count debris smaller than 1 µm and/or greater than 100 µm, if desired. Lubricant monitoring system 38 may report particle data in any suitable format, such as a number of particles of a certain size per milliliter of lubricant. Alternatively, concentrations of debris particles may be reported as numbers of a code system provided by the International Organization for Standardization (ISO). ISO code numbers may indicate a particular distribution or range of concentrations in which the measured concentration is included for a given size of debris particle. In other embodiments, lubricant monitoring system 38 may include an electromagnetic sensor, dielectric sensor, or other type of sensor for determining a concentration of debris particles in the lubricant or other important lubricant parameters.

Gearbox monitoring system 30 may also include a temperature sensor 40 configured to generate a signal indicative of a temperature associated with the lubricant and/or rotational components within gearboxes 22-26. For example, temperature sensor 40 may be immersed within gearbox lubricant and configured to determine a lubricant temperature. In some embodiments, the lubricant temperature may be used to determine a temperature of rotational components within gearboxes 22-26. Temperature sensor 40 may also or alternatively be associated with individual rotational components within gearboxes 22-26 to directly measure the temperature of the rotational components. In some embodiments, temperature sensor 40 may be combined with or form a single sensor unit with lubricant monitoring system 38.

Gearbox monitoring system may also include a load sensor 42 configured to generate a signal indicative of a vertical load $L_V$ on one or more of gearboxes 22-26 and/or rotational components therein. Load sensor 42 may be associated with suspension device 21 and configured to measure the vertical load $L_V$ transferred to gearboxes 22-26 from frame 12 through suspension device 21. For example, load sensor may be a position sensor disposed internally or externally of suspension device 21 that is configured to measure a displacement of suspension device 21 with respect to a reference position or a fluid pressure therein. The signal generated by load sensor 42 may be calibrated to indicate the vertical load (e.g., payload weight, weight of frame, jolting force, etc.) experienced by gearboxes 22-26. In other embodiments, load sensor 42 may be a force or pressure transducer, such as a load cell, a strain gauge, a pressure transducer, or other sensory device configured to measure the downward force applied to gearboxes 22-26 through suspension device 21.

Gearbox monitoring system 30 may include one or more additional sensors 44 configured to generate signals indicative of environmental and/or other machine parameters. For example, sensors 44 may include an ambient temperature sensor, humidity sensor, inclinometer, throttle position sensor, fuel flow sensor, etc. Signals generated by sensors 44 may be indicative of additional loads experienced by gearboxes 22-26 and rotational components therein.

Controller 46 may be configured to determine the remaining lifetime $\theta_R$ of at least one rotational component within gearboxes 22-26 (e.g., at least one shaft, bearing, gear, etc.). Controller 46 may be configured to determine the remaining lifetime $\theta_R$ of the at least one rotational component based on the design lifetime $\theta_D$ of the rotational component, at least one design parameter of the rotational component, and the signals generated by one or more of sensors 32-36, 40-44 and lubricant monitoring system 38 over a period of operating time. Controller 46 may also be configured to generate a maintenance signal based on the remaining lifetime.

Controller 46 may embody a one or more microprocessors, computers, and/or modules that may be contained within a single enclosure or located some distance from each other. Numerous commercially available microprocessors, computers, and/or modules can be configured to perform the functions of controller 46. It should be appreciated that controller 46 could readily embody a general machine controller capable of controlling numerous machine functions. Controller 46 may also include a memory (e.g., RAM, ROM, flash disk, hard drive, CD, DVD, magnetic disk or tape, etc.) for storing data, models, algorithms, maps, and other types of data, instructions, and information. Various other circuits may be associated with controller 46, including power supply circuitry, signal-conditioning circuitry, solenoid driver circuitry, communication circuitry, and other appropriate circuitry.

Controller 46 may store within its memory design parameters and other information associated with the rotational components within gear boxes 22-26. Design parameters may include operating parameters (e.g., torque, speed, temperature, humidity, radial force, number of vibrations, etc.) that the rotational components within gear boxes 22-26 may be designed to withstand during a corresponding design lifetime (e.g., number of hours, number of miles, number of days, number of years, etc.). Design parameters may be single fixed values, value ranges, or average values (i.e., values representing average operating parameters over a period of time).

The design lifetime $\theta_D$ of a rotational component may represent an allowable period of operating time until a respective rotational component requires maintenance and/or replacement. The design lifetime $\theta_D$ of a rotational component may be a function of operating time spent under the design parameters. That is, a rotational component having a design lifetime $\theta_D$ of, for example 2000 hours, may be expected to require maintenance or replacement after operating for 2000 hours at its respective design speed $s_D$, design torque $\tau_D$, design load $L_D$, and/or other design parameters. When one or more of gearboxes 22-26 include multiple rotational components, the shortest design lifetime $\theta_D$ among the rotational components may be equal to a design lifetime $\theta_D$ of the respective gearbox 22-26 and represent a shortest anticipated time until maintenance or repair may be needed.

Other information associated with the rotational components within gear boxes 22-26 may include numbers of gears, gear ratios, gear dimensions, bearing dimensions, shaft dimensions, etc. When gear boxes 22-26 have multiple selectable gears, controller 46 may store a gear ratio associated with each possible gear setting or gear combination. Information associated with the rotational components of gearboxes 22-26 may be stored within controller 46 during assembly of machine 10 and may be updated by a service technician or other personal via a computerized connection.

Because actual operating parameters are not always equal to the design parameters of the rotational component, the remaining lifetime $\theta_R$ of a rotational component may not be accurately determined by subtracting an amount of operating time from the design lifetime $\theta_D$. That is, the actual operating parameters may be higher or lower than the design parameters depending on varying operating practices of one or more machine operators, varying ambient conditions, varying jobsite conditions, etc., which may increase or reduce the amount of time until maintenance or replacement of the rotational component is needed. As a result, unexpected or unnecessary maintenance may be carried out, which can reduce the overall efficiency of an operation.

To help facilitate efficient maintenance and repair scheduling, controller 46 may determine the remaining lifetime $\theta_R$ of a rotational component based on the design lifetime $\theta_D$ and at least one design parameter of the rotational component in conjunction with the signals generated by one or more of sensors 32-36,40-44 and lubricant monitoring system 38 over a period of operating time. For example, controller 46 may continually determine one or more ratios of actual operating parameters to design parameters over a sample period time interval $\Delta t$ and determine a normalized fraction $\theta_C$ of the design lifetime $\theta_D$ that has been consumed. When actual operating parameters are not equal to the design parameters, the normalized fraction $\theta_C$ of the design lifetime $\theta_D$ that has been consumed and the remaining lifetime $\theta_R$ of the rotational component may be determined using EQ1 and EQ2 below:

$$\theta_C = \Sigma\left[\left[\left(\frac{\tau}{\tau_D}\right)^x \times \left(\frac{s}{s_D}\right)^y \times \left(\frac{\Delta t}{\theta_D}\right)\right]/C\right] \quad \text{EQ 1}$$

$$\theta_R = (1 - \theta_C) \times \theta_D \quad \text{EQ 2}$$

where x, y, and C are constants determined empirically. It is understood that other or additional design parameters may be incorporated into EQ1, if desired. As shown in EQ1 and EQ2, controller 46 may be configured to determine the remaining lifetime $\theta_R$ based on one or more of a ratio of the speed s associated with the rotational component to the design speed $s_D$ and a ratio of the torque $\tau$ associated with the rotational component to the design torque $\tau_D$. Controller 46 may also determine the remaining lifetime $\theta_R$ based on a ratio of the sample period time interval $\Delta t$ to the design life $\theta_D$. It is understood that other or additional ratios associated with other or additional parameters may be used, if desired.

When the actual operating parameters (e.g., actual torque $\tau$, actual speed s, etc.) do not equal the design parameters (e.g., $\tau_D$, $s_D$, etc.), controller 46 may use EQ1 to determine a cumulative sum of normalized fractions $\theta_C$ of the design lifetime $\theta_D$ consumed over one or more time intervals $\Delta t$. Controller 46 may then use EQ2 to determine the remaining lifetime $\theta_R$ of the rotational component with respect to its design lifetime $\theta_D$ based on the cumulative sum determined in EQ1. In this way, as the actual torque $\tau$ and speed s vary in response to variations in the severity of usage of machine 10 during operation, the remaining lifetime $\theta_R$ of rotational components within gearboxes 22-26 may be determined more accurately, thereby allowing provisional maintenance schedules to be adjusted to earlier or later dates as needed. This may improve the overall efficiency of operations by prolonging the use of parts that have not yet been fully worn while curtailing the use of prematurely worn parts before unexpected failures occur.

Controller 46 may also be configured to determine the remaining lifetime $\theta_R$ of certain rotational components associated with drive system 16, such as wheel bearings (not shown), that experience multifaceted radial loads L. For example, the weight of frame 12, the payload carried by machine 10, and/or other forces may contribute a vertical load $L_V$ on certain rotational components. The vertical load $L_V$ may include forces caused by gravity and/or changes in vertical movements of machine 10 (e.g., when machine 10 is jolted up and down while traveling over rugged surfaces). Additional loads may include a tractive effort load $L_T$ that may be associated with the torque $\tau$ used to drive machine 10 and/or the forces used to slow machine 10. The tractive effort load $L_T$ may include forces experienced by rotational components in a direction parallel to the travel direction of machine 10. Accordingly, controller 46 may be configured to determine the radial load L on a rotational component based in part on a combination of loads, such as the vertical load $L_V$ and/or the tractive load $L_T$, as a vector sum using EQ3 below:

$$L = \sqrt{(L_V)^2 + (L_T)^2}. \quad \text{EQ3:}$$

Although EQ3 shows one way of determining the magnitude of radial load L based on $L_V$ and $L_T$, it is understood that different equations may be used to determine radial load L. For example, when $L_V$ and $L_T$ are not perpendicular, angles that separate $L_V$ and $L_T$ from each other and/or from reference planes or axes may be determined and used to calculate the magnitude of radial load L. Radial load L is understood to be the total radial force acting on a rotational component 22-26 and may therefore be calculated according to sensor configurations, orientation of machine 10, and/or other geometric considerations.

Controller 46 may be configured to determine the vertical load $L_V$ based on the signal generated by load sensor 42. A signal from load sensor(s) 42 may be received in association with one or more of traction devices 18, allowing for the effects on rotational component wear due to uneven payload distributions within machine 10, which can cause components on one side (e.g., left, right, front, rear) to wear out faster than the others, may be accounted for. In other embodiments, controller 46 may also or alternatively be configured to determine the vertical load $L_V$ based on known weights, payloads, and inclines on which machine 10 travels. For example, weight and/or payload values may be stored within controller 46, received via one or more scale readings, and/or received via an input device associated with operator station 20 or communication device 50. The weight information may be used in conjunction with signals from other sensors, such as an inclinometer, by controller 46 to determine the vertical load $L_V$. Other ways of determining the vertical load $L_V$ may be possible.

Controller 46 may be configured to determine the tractive load $L_T$ based on the signal from torque sensor 36 and/or other sensors. That is, tractive load $L_T$ may be a function of the torque τ, as determined by controller 46 based on the signal from torque sensor 36. The tractive load $L_T$ may also be a function of dimensions of traction devices 18, such as a radius or diameter. In some embodiments, tractive load $L_T$ may be equal to the rimpull torque experienced at traction devices 18.

When drive system 16 includes rotational components that bear radial loads L, controller 46 may be configured to determine the remaining lifetime $\theta_R$ of the rotational components based on a ratio of the radial load L to the design load $L_D$. In one embodiment, for example, controller 46 may be configured to determine the remaining lifetime $\theta_R$ of the rotational components based on one or more of a ratio of the radial load L to the design load $L_D$ and a ratio of the speed s associated with the rotational components to the design speed $s_D$, as shown in EQ4 below:

$$\theta_C = \Sigma\left[\left[\left(\frac{L}{L_D}\right)^x \times \left(\frac{s}{s_D}\right)^y \times \left(\frac{\Delta t}{\theta_D}\right)\right]/C\right]. \quad \text{EQ 4}$$

where x, y, and C are constants determined empirically. It should be noted that values for x, y, and/or C may be different than in EQ1.

Controller 46 may determine the normalized fraction $\theta_C$ of the design lifetime $\theta_D$ that has been consumed and the remaining lifetime $\theta_R$ of the rotational component using EQ4 and EQ2 above. It is understood that other or additional factors may be used in conjunction with EQ4, if desired.

EQ1 may be particularly applicable to gears, whereas EQ4 may be particularly applicable to bearings. Controller 46 may be configured to compare the results of EQ2 (using the results of EQ1 as an input) with the results of EQ2 (using the results of EQ4 as an input) to arrive at a total remaining lifetime $\theta_T$. The total remaining lifetime $\theta_T$ may be indicative of the shortest amount of time until one of gearboxes 22-26 is expected to require maintenance or replacement. In this way, the wearing of rotational components due to additional factors, such as traveling over inclines, declines, rough terrain, etc., may be accounted for and used to more accurately determine the remaining lifetime $\theta_R$ of rotational components within gearboxes 22-26, as well as whether the total remaining lifetime $\theta_T$ of gearboxes 22-26 is greater than or less than an amount of time until the next regularly scheduled service appointment of machine 10.

Based on the total remaining lifetime $\theta_T$, provisional maintenance schedules may be adjusted to earlier or later dates as needed, which may improve the overall efficiency of operations by prolonging the use of parts that have not yet been fully worn while curtailing the use of prematurely worn parts before unexpected failures occur.

Controller 46 may also be configured to receive and/or store additional information relevant to the condition of gearboxes 22-26 and/or their respective rotational components and lubricant. For example, controller 46 may be configured to receive prior service information via communication device 50 or another suitable data transfer interface. Prior service information may include lubricant change information (e.g., date, time, type, quantity, specifications, quality factor, etc.), gear and bearing information (e.g., replacement date and time, serial number, gear or bearing type, dimensions, quality factor, etc.), and/or the design parameters associated with the lubricant and each rotational component. Controller 46 may be configured to determine the total remaining lifetime $\theta_R$ of the rotational components associated with gearboxes 22-26 based on the prior service information. For example, controller 46 may be configured to determine a service history factor ω based on the prior service information and apply the service history factor ω to the remaining lifetime $\theta_R$ of the rotational components. The service history factor ω may be a constant determined based on the age, quality, and/or other service information of each rotational component and the lubricant of gearboxes 22-26. Other factors may be used to determine the service history factor ω, if desired.

Controller 46 may also be configured to determine the remaining lifetime $\theta_R$ of the rotational components associated with gearboxes 22-26 based on the signal from lubricant monitoring system 38 indicative of the lubricant condition. For example, based on the signal from lubricant monitoring system 38 in conjunction with one or more additional parameters, such as the torque τ, speed s, temperature (e.g., ambient, of final drive 26, etc.), a lubricant parameter (e.g., temperature, viscosity, pressure, etc.), and/or other data, controller 46 may determine a lubricant factor ∈ that may be applied to the remaining lifetime $\theta_R$ determined using EQs 1-4 above. Controller 46 may determine the lubricant factor ∈ using a mathematical function derived empirically or by modeling. The mathematical function may include models, algorithms, maps, and/or other functions that relate particle debris concentrations of certain sized particles to the remaining lifetime $\theta_R$ of the rotational components and/or of the lubricant. The mathematical functions may be derived using controlled testing, such as by measuring particle concentrations under a variety of operating parameters and formulating maps and/or or equations relating the particle concentrations to the operating parameters. The mathematical functions may also or alternatively be generated using modeling methods, such as finite element methods, and/or other means for estimating current and future particle levels from sensed operating parameters.

Offboard computer 48 may embody an electronic device configured to process and/or display data to maintenance personnel, site managers, fleet managers, etc. For example, offboard computer 48 may include one or more microprocessors, data storage components, memory, a computer, a portable communication device configured to process and/or transmit data (e.g., a cellular phone, a tablet, laptop computer, etc.) etc. Offboard computer 48 may be connected to controller 46 via a network configured to exchange data (e.g., cellular network, LAN, CAN, data bus, Ethernet, Internet, telephone, satellite, etc.). Offboard computer 48 may also include a user interface (e.g., a keyboard, touch screen, soft keys, etc.) configured to receive operator inputs that may be stored as data and/or transmitted to controller 46 via the communication network.

Communication device 50 may include any device that facilitates communication of data between machine 10 and offboard computer 48. Communication device 50 may include hardware and/or software that enables sending and/or receiving data through a wireless communication link, a direct data link, or by a voice commination device, such as a two-way radio. In some cases, communication device 50 may include a portable data recording medium, and data may be transferred from machine 10 to offboard computer 48 using the portable data recording medium.

INDUSTRIAL APPLICABILITY

The disclosed monitoring system may be used in any machine that employs one or more gearboxes that contain rotational components and/or a lubricant, where it is beneficial to estimate a remaining lifetime of the gearbox, its rotational components, or the lubricant contained therein. The disclosed monitoring system finds particular applicability within mobile machines having gearboxes that require periodic maintenance caused by wearing and/or failure of rotational components under various operating parameters. Exemplary operations of monitoring system 30 will now be described.

Prior to operation of machine 10, such as when machine 10 is assembled or during a most recent maintenance procedure, machine 10 may receive prior service information via communication device 50 or another suitable data interface. At this same time, the design parameters of the rotational components and/or lubricant of gearboxes 22-26 may be received via communication device 50 or another suitable data interface. The prior service information and design parameters may be stored within the memory of controller 46 and used for further processing.

During operation of machine 10, controller 46 may receive machine and environmental data from one or more of sensors 32-44. As operating practices, environmental conditions, worksite conditions, payload conditions, and/or other factors vary throughout the operation of machine 10 with respect to the design parameters of the rotational components of gearboxes 22-26, controller 46 may receive data from sensors 32-36, 40-44 and lubricant monitoring system 38 that may be used to determine the remaining lifetime $\theta_R$ of the rotational components For example, as operating practices of machine 10 vary (e.g., during a shift, from one shift to another, etc.), one or more of sensors 32-36, 40-44 and lubricant monitoring system may detect variations of operating parameters from respective design parameters. For instance, variations in the severity with which operators control movements of machine 10 may be reflected in the data generated by speed sensors 32 and 34, torque sensor 36, and/or load sensor 42. When machine 10 is operated at faster speeds, with greater accelerations and decelerations, and with greater loads on more rugged terrains, the rotational components and lubricant within gearboxes may be caused to wear out faster. By accounting for variations in operating practices, more accurate determinations of whether the rotational components will fall short of or exceed their design lifetimes $\theta_D$ can be made.

Additionally, as environmental conditions and operating practices vary, data received from lubricant monitoring system 38 and/or temperature sensor 40 may be indicative of the condition of the lubricant within gearboxes 22-26 and whether maintenance will be required before or after the design lifetime $\theta_D$. For example, higher operating temperatures and/or higher particle concentrations within the lubricant may indicate that the lubricant should be changed or that it is safe to continue operation for a longer period of time. Higher temperatures and particle concentrations may also be indicative of sudden and/or severe damage that has occurred to gearboxes 22-26, which may require immediate attention and or decommissioning of machine 10.

When machine 10 is filled with heavier payloads, greater vertical loads $L_V$ on rotational components that more rapidly decease the remaining lifetime $\theta_R$ of rotational components may be detected by load sensor 42. As worksite surfaces become more rugged (and as operators drive faster), load sensor 42 may generate signals indicative of greater vertical loads $L_V$ in response to greater jolting forces (e.g., due to more and/or larger potholes, washboarding, etc.). Worksites having sections with steep grades may cause the weight of machine 10 to shift, causing greater vertical loads on some rotational components and less on others. As a result, some rotational components may wear out and require replacement sooner than others. During weight shifts, such as when machine 10 is on an incline or decline, a portion of vertical load $L_V$ may be converted to tractive load $L_T$, thereby increasing wear on rotational components as a function of torque $\tau$. Increases in tractive load $L_T$ may also occur when machine 10 is operated at greater speeds (e.g., on flat and graded surfaces), as indicated by signals from torque sensor 36 and/or load sensor 42.

As environmental conditions vary, wear on rotational components within gearboxes 22-26 may increase or decrease. Signals generated by sensors 44 may be indicative of environmental parameters, such as temperature, humidity, barometric pressure, ambient light, etc., which may be indicative of how rapidly rotational components and the lubricant within gearboxes 22-26 are wearing.

After receiving data from sensors 32-44, controller 46 may then determine the normalized fraction $\theta_C$ of the design lifetime $\theta_D$ that has been consumed and the remaining lifetime $\theta_R$ of gears within gearboxes 22-26 using EQ1 and EQ2. Controller 46 may also determine the normalized fraction $\theta_C$ of the design lifetime $\theta_D$ that has been consumed and the remaining lifetime $\theta_R$ of bearings within gearboxes 22-26 using EQ2, EQ3, and EQ4. Controller 46 may then apply the service history factor $\omega$ and/or the lubricant factor $\in$ to the results of EQ2 (as used in conjunction with the results of EQ1 and EQ4) and determine the total remaining lifetime $\theta_T$ of gearboxes 22-26. Controller 46 may determine how much time and/or mileage has elapsed since machine 10 was previously serviced and compare the elapsed time and/or mileage to the total remaining lifetime $\theta_T$ and determine whether there is a need to perform maintenance on gearboxes 22-26 before a next regularly scheduled maintenance date.

Controller 46 may generate a maintenance signal based on the total remaining lifetime $\theta_T$. That is, controller 46 may generate a signal indicative of the total remaining lifetime $\theta_T$ (e.g., expressed in time, mileage, etc.), which may be accessed by maintenance personnel via communication device 50 or another suitable data transfer interface. The maintenance signal may be indicative of a need to perform gearbox maintenance before a threshold time period will elapse, such as a time until the next regularly scheduled maintenance date. The maintenance signal may be configured to be displayed via a diagnostic machine or another type of computer. When displayed, the maintenance signal may be shown as one or more indicia, such as a percent likelihood or probability, a sliding bar (e.g., a bar indicating a health level between full and empty), a color code (e.g., green, yellow, and red indicia), and or another type of indicia. In some embodiments, the maintenance signal may also be shown to an operator of machine 10 via a display associated with operator station 20.

Several advantages may be realized by the implementation of gearbox monitoring system 30. In particular, because monitoring system 30 may account for the wearing of rotational components as well as lubricant within gearboxes 22-26, a more accurate determination of the total remaining lifetime of gearboxes 22-26 may be made. Also, because monitoring system 30 may determine the remaining lifetime of rotational components based on the design lifetime, design parameters, and actual operating parameters, varying factors, such as worksite conditions, ambient conditions, and operator control of machine 10, may be accounted for when determining the total remaining lifetime $\theta_T$ of gearboxes 22-26. As a result, more efficient and convenient machine maintenance schedules may be made, resulting in more efficient overall operations.

It will be apparent to those skilled in the art that various modifications and variations can be made to the disclosed monitoring system. Other embodiments will be apparent to those skilled in the art from consideration of the specification and practice of the disclosed monitoring system. It is intended that the specification and examples be considered as exemplary only, with a true scope being indicated by the following claims and their equivalents.

What is claimed is:

1. A monitoring system for a gearbox having at least one rotational component with a design lifetime and a plurality of design parameters, the monitoring system comprising:
   a first sensor configured to generate a first signal indicative of a rotational speed associated with the at least one rotational component;
   a second sensor configured to generate a second signal indicative of a torque associated with the rotational component; and
   a controller electronically connected to the first and second sensors and configured to:
      determine a remaining lifetime of the at least one rotational component based on the design lifetime, the plurality of design parameters, and the first and second signals over a period of operating time, wherein the plurality of design parameters includes a design torque and a design speed of the rotational component; and
      generate a maintenance signal based on the remaining lifetime,
   wherein the maintenance signal is indicative of a need to perform gearbox maintenance before a threshold time period will elapse.

2. The monitoring system of claim 1, wherein the controller is configured to determine the remaining lifetime based on one or more of a ratio of the speed associated with the at least one rotational component to the design speed and a ratio of the torque associated with the at least one rotational component to the design torque.

3. The monitoring system of claim 1, wherein:
   the monitoring system further includes a third sensor electronically connected to the controller and configured to generate a third signal indicative of a vertical load on the at least one rotational component; and
   the controller is configured to determine a radial load on the at least one rotational component based on the third signal; and
   the controller is further configured to determine the remaining lifetime of the at least one rotational component based on the radial load.

4. The monitoring system of claim 3, wherein the controller is configured to:
   determine a tractive load on the at least one rotational component based on the second signal; and
   determine the radial load on the at least one rotational component based in part on the tractive load.

5. The monitoring system of claim 4, wherein:
   the design parameter is one or more of a design load and a design speed; and
   the remaining lifetime of the at least one rotational component is determined based on one or more of a ratio of the radial load to the design load and a ratio of the speed associated with the at least one rotational component to the design speed.

6. The monitoring system of claim 1, wherein:
   the monitoring system further includes a lubricant monitoring system configured to generate a signal indicative of a lubricant condition; and
   the controller is configured to determine the remaining lifetime of the at least one rotational component based on the lubricant condition.

7. The monitoring system of claim 6, wherein the lubricant monitoring system includes one or more of a temperature sensor and a particle sensor.

8. The monitoring system of claim 7, wherein the particle sensor is one or more of an optical sensor and an electromagnetic sensor.

9. A method of monitoring a gearbox having at least one rotational component having a design lifetime and a plurality of design parameters, the method comprising:
   receiving a first signal from a first sensor electronically connected to a controller and determining, via the controller, a rotational speed associated with the at least one rotational component based on the first signal;
   receiving a second signal from a second sensor electronically connected to the controller and determining, via the controller, a torque associated with the rotational component based on the second signal;
   determining, via the controller, a remaining lifetime of the at least one rotational component based on the design lifetime, the plurality of design parameters, and the rotational speed and the torque associated with the at least one rotational component over a period of operating time, wherein the plurality of design parameters includes a design torque and a design speed of the rotational component; and
   generating, via the controller, a maintenance signal based on the remaining lifetime, wherein the maintenance signal is indicative of need to perform gearbox maintenance before a threshold time period will elapse.

10. The method of claim 9, wherein the remaining lifetime is determined based on one or more of a ratio of the speed associated with the at least one rotational component to the design speed and a ratio of the torque associated with the at least one rotational component to the design torque.

11. The method of claim 9, further including:
   determining a vertical load on the at least one rotational component;
   determining a radial load on the at least one rotational component based on the vertical load; and
   determining the remaining lifetime of the at least one rotational component based on the radial load.

12. The method of claim 11, further comprising:
   determining a tractive load on the at least one rotational component; and
   determining the radial load on the at least one rotational component based in part on the tractive load.

13. The method of claim 12, wherein:
the design parameter is one or more of a design load and a design speed; and
the remaining lifetime of the at least one rotational component is determined based on one or more of a ratio of the radial load to the design load and a ratio of the speed associated with the at least one rotational component to the design speed.

14. The method of claim 9, further including:
determining a lubricant condition; and
determining the remaining lifetime of the at least one rotational component based on the lubricant condition.

15. The method of claim 14, wherein determining the lubricant condition includes determining one or more of a lubricant temperature and a concentration of debris particles.

16. A monitoring system for a gearbox having at least one rotational component having a design lifetime and a plurality of design parameters, the monitoring system comprising:
a first sensor configured to generate a first signal indicative of a rotational speed associated with the at least one rotational component;
a second sensor configured to generate a second signal indicative of a torque associated with the rotational component;
a third sensor configured to generate a third signal indicative of a vertical load on the at least one rotational component; and
a controller electronically connected to the first, second, and third sensors and configured to:
determine a remaining lifetime of the at least one rotational component based on the design lifetime, the plurality of design parameters, and the first, second, and third signals over a period of operating time, wherein the plurality of design parameters includes a design torque, a design speed, and a design load of the rotational component; and
generate a maintenance signal based on the remaining lifetime,
wherein the maintenance signal is indicative of a need to perform gearbox maintenance before a threshold time period will elapse.

* * * * *